United States Patent
Calvert

(10) Patent No.: US 10,646,661 B2
(45) Date of Patent: May 12, 2020

(54) NEEDLE ASSEMBLY WITH NEEDLE SHROUD AND MOVABLE NEEDLE SUPPORT

(71) Applicant: Owen Mumford Limited, Oxford (GB)

(72) Inventor: Jack Calvert, Oxford (GB)

(73) Assignee: Owen Mumford Limited, Oxford (GB)

(*) Notice: Subject to any disclaimer, the term of this patent is extended or adjusted under 35 U.S.C. 154(b) by 234 days.

(21) Appl. No.: 15/507,442

(22) PCT Filed: May 10, 2016

(86) PCT No.: PCT/GB2016/051334
§ 371 (c)(1),
(2) Date: Feb. 28, 2017

(87) PCT Pub. No.: WO2016/181127
PCT Pub. Date: Nov. 17, 2016

(65) Prior Publication Data
US 2018/0064883 A1 Mar. 8, 2018

(30) Foreign Application Priority Data

May 11, 2015 (GB) .................................. 1507981.7
Oct. 21, 2015 (GB) .................................. 1518649.7

(51) Int. Cl.
*A61M 5/32* (2006.01)
(52) U.S. Cl.
CPC .......... *A61M 5/3202* (2013.01); *A61M 5/321* (2013.01); *A61M 5/3213* (2013.01);
(Continued)
(58) Field of Classification Search
CPC .............. A61M 5/3213; A61M 5/3243; A61M 5/3245; A61M 5/3257; A61M 2005/3267; A61M 2005/3247
See application file for complete search history.

(56) References Cited

U.S. PATENT DOCUMENTS 6,203,529 B1 * 3/2001 Gabriel ............... A61M 5/3202
604/192
2003/0014018 A1 1/2003 Giambattista
(Continued)

FOREIGN PATENT DOCUMENTS

CN 1467001 A 1/2004
EP 1949928 7/2008
(Continued)

OTHER PUBLICATIONS

International Search Report and Written Opinion issued in corresponding PCT Application No. PCT/GB2016/051334, dated Aug. 11, 2016, 6 pages.
(Continued)

Primary Examiner — Rebecca E Eisenberg
Assistant Examiner — Tasnim Mehjabin Ahmed
(74) Attorney, Agent, or Firm — Quarles & Brady LLP

(57) ABSTRACT

A needle assembly for mounting on an injection device which comprises a body configured to be attached to an injection device in use; a double ended needle; and a needle shield coupled to the body. The needle shield is arranged for axial movement with respect to the body. The needle assembly has an injection configuration, in which the shield is positioned such that the forward tip of the needle projects beyond a forward end of the shield. The needle assembly also has a shroud configuration, in which the shield is positioned such that the forward end of the shield extends beyond the forward tip of the needle. The needle assembly further comprises a needle support fixed relative to the body when the needle assembly is in the injection configuration. Movement of the shield from the injection configuration to the shroud configuration axially displaces the needle support relative to the body.

20 Claims, 12 Drawing Sheets

(52) U.S. Cl.
CPC ........ *A61M 5/3243* (2013.01); *A61M 5/3245* (2013.01); *A61M 5/3257* (2013.01); A61M 2005/3254 (2013.01)

(56) References Cited

U.S. PATENT DOCUMENTS

| | | | |
|---|---|---|---|
| 2008/0177237 A1* | 7/2008 | Stonehouse | A61M 5/326 604/263 |
| 2011/0178473 A1* | 7/2011 | Richards | A61M 5/3257 604/198 |
| 2014/0288504 A1 | 9/2014 | Karlsson et al. | |

FOREIGN PATENT DOCUMENTS

| | | |
|---|---|---|
| EP | 1949929 | 7/2008 |
| EP | 2883563 | 12/2013 |
| JP | 2008220934 A | 9/2008 |
| JP | 2013500745 A | 1/2013 |
| TW | 200735908 A | 10/2007 |
| WO | 2009/102612 | 8/2009 |
| WO | 2010/147552 | 12/2010 |
| WO | 2011/078851 | 6/2011 |
| WO | 2014/068098 | 5/2014 |

OTHER PUBLICATIONS

Search Report issued in corresponding United Kingdom Application No. GB 1507981.7, dated Oct. 29, 2015, 4 pages.
Search Report issued in corresponding United Kingdom Application No. GB 1518649.7, dated Dec. 7, 2015, 3 pages.
Notice of Allowance issued in corresponding Korean Patent Application No. 10-2017-7010811, dated Feb. 26, 2018, 3 pages.
Office Action issued in corresponding Taiwanese Patent Application No. 105110807, dated Jul. 5, 2018, 12 pages.

* cited by examiner

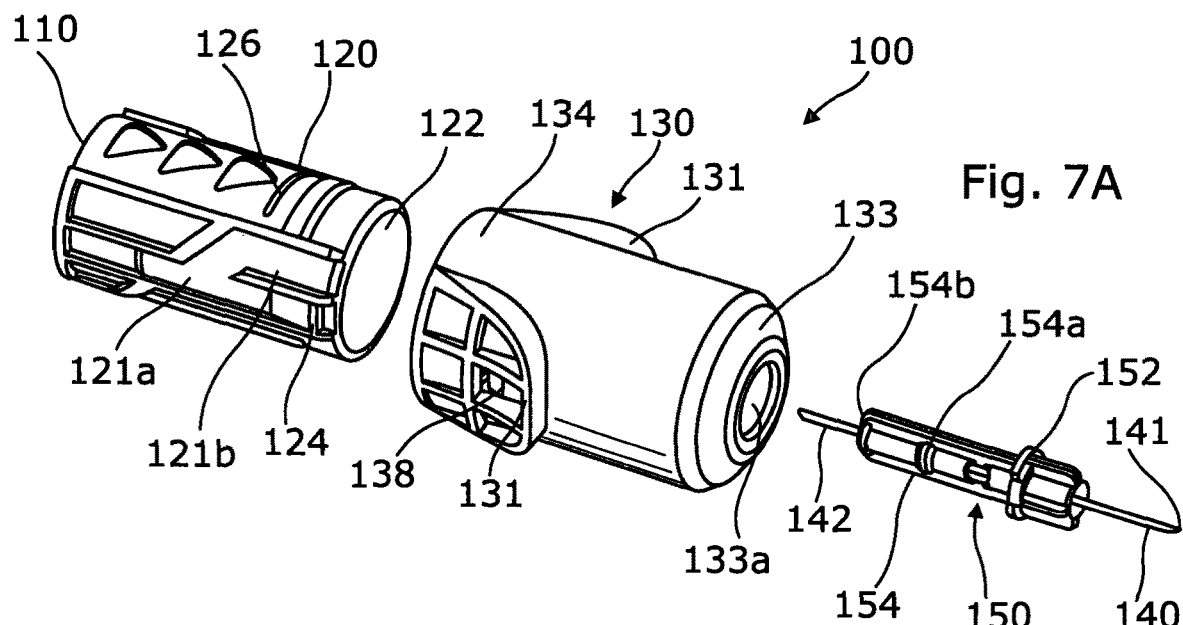
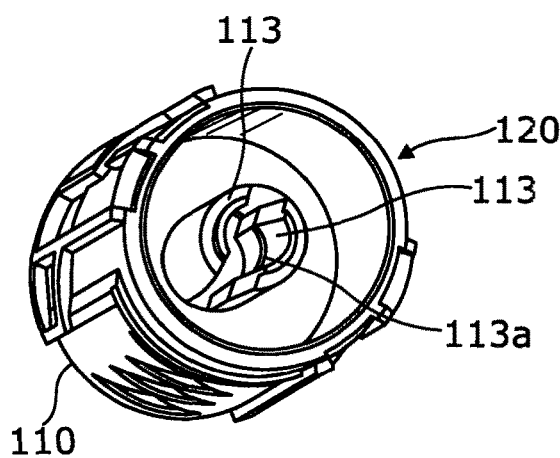
Fig. 7A
Fig. 7B
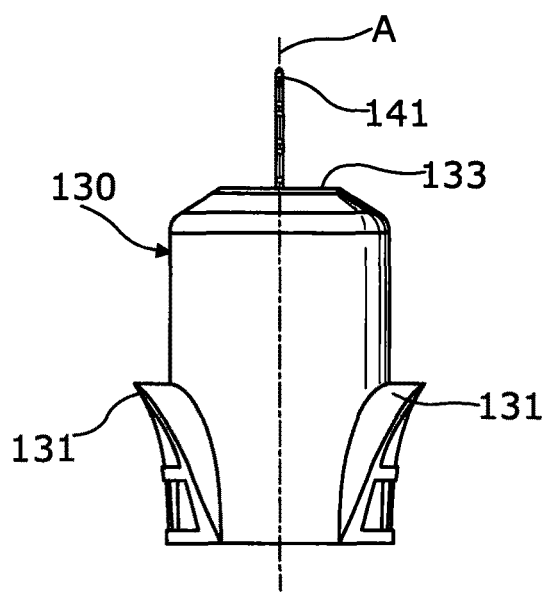
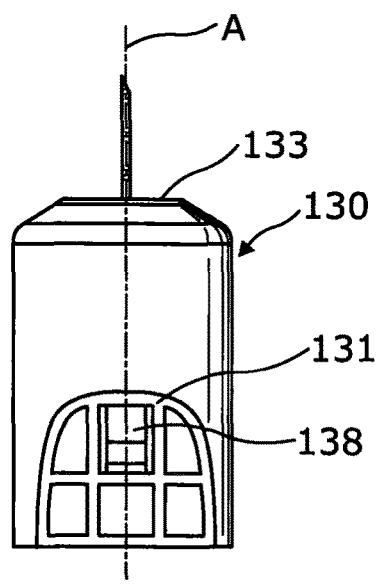
Fig. 8A                Fig. 8B

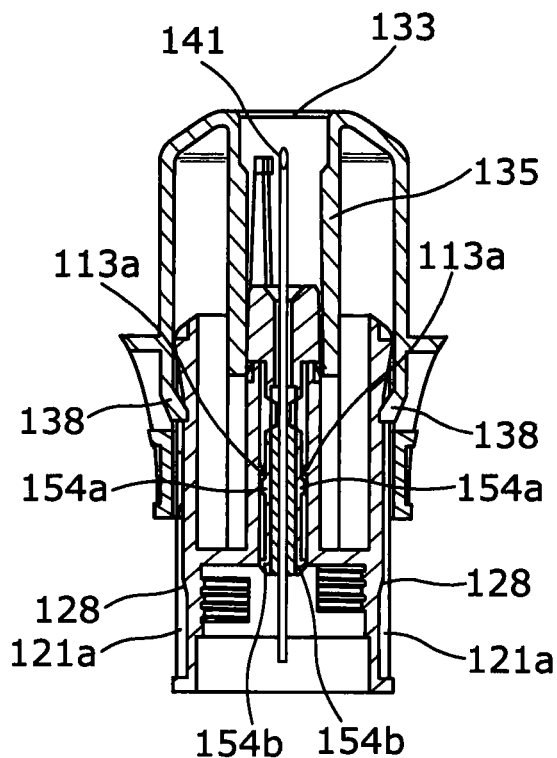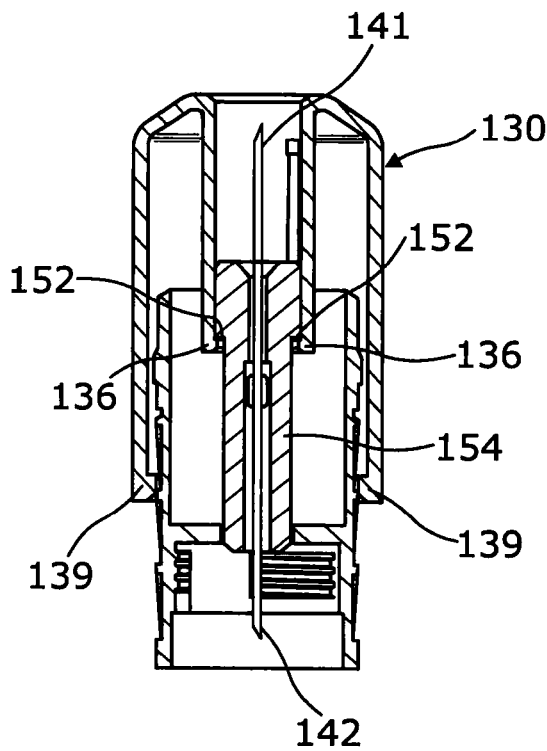
Fig. 11A　　Fig. 11B
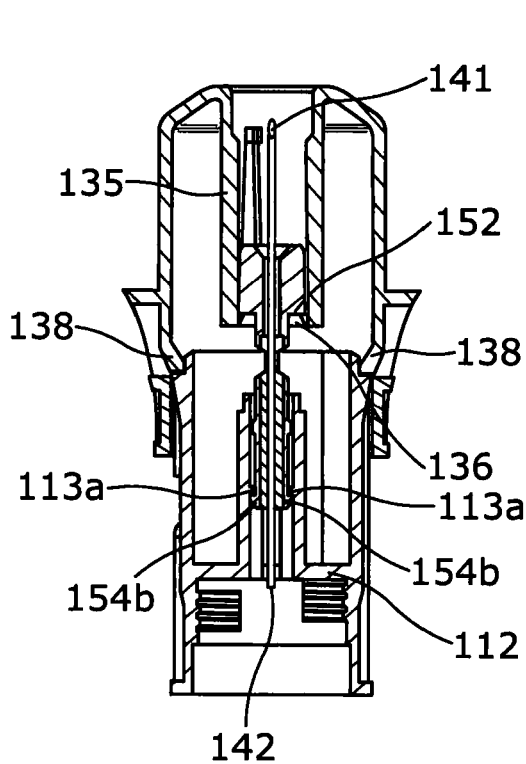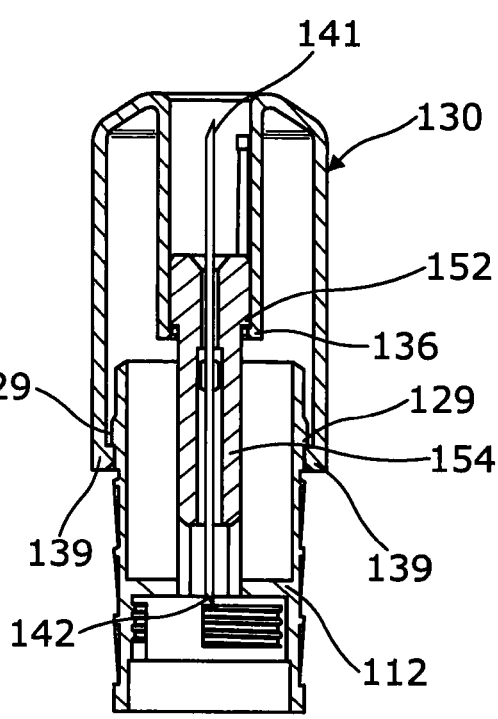
Fig. 12A　　Fig. 12B

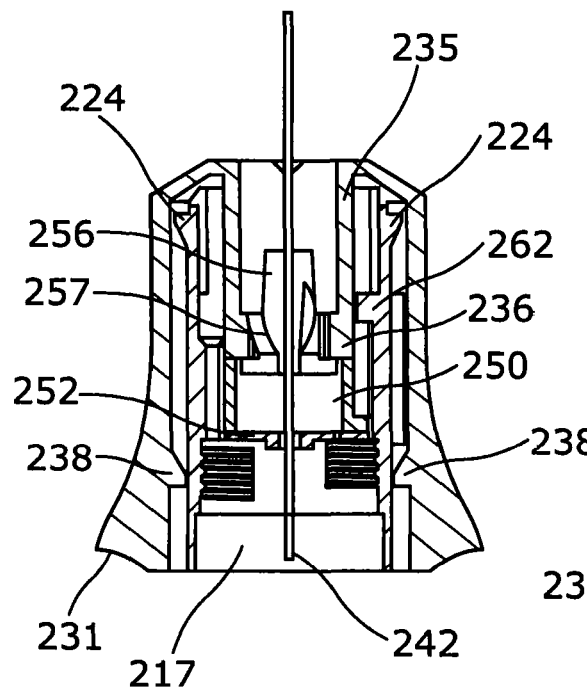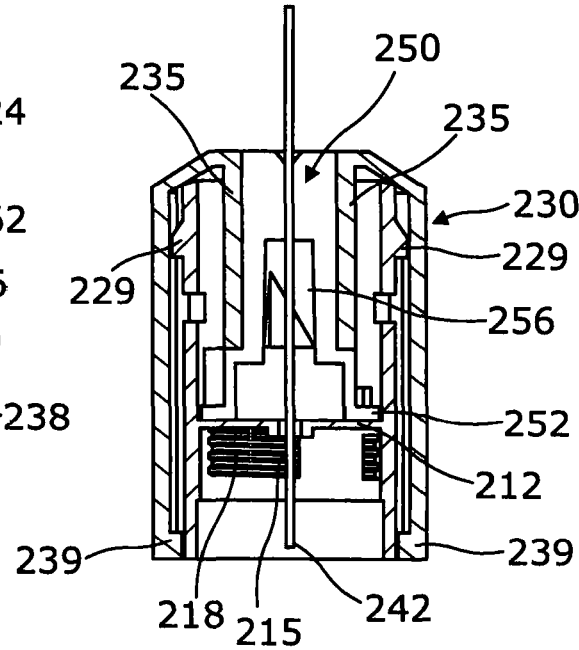
Fig. 16A  Fig. 16B
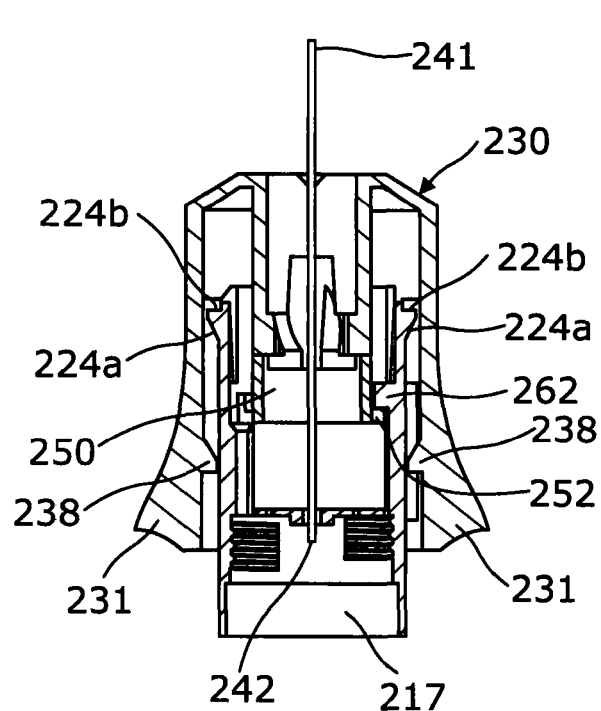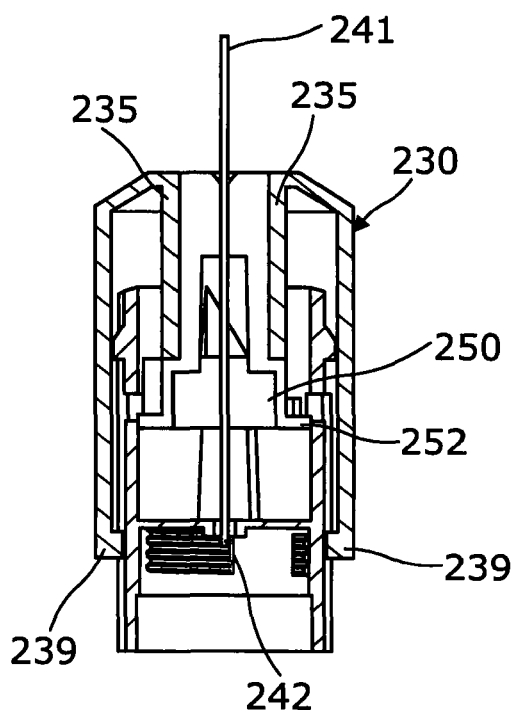
Fig. 17A  Fig. 17B

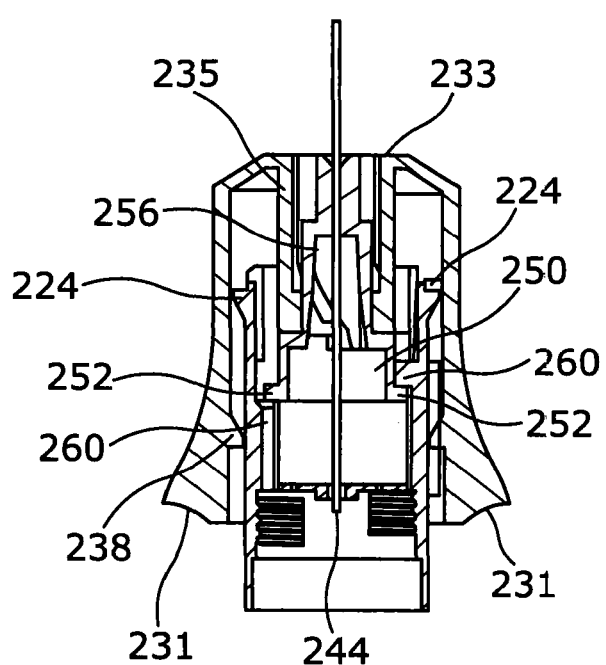
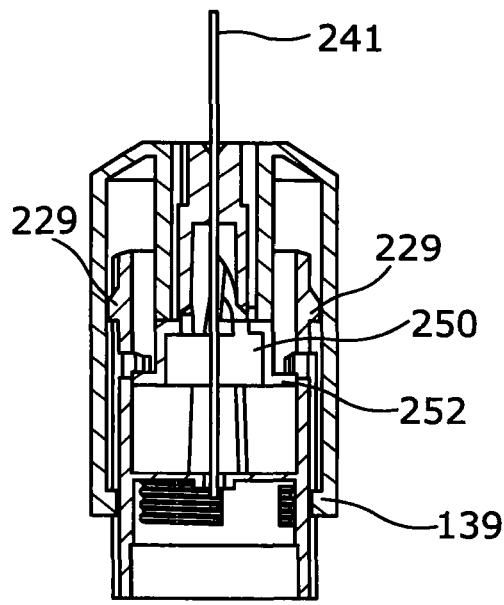
Fig. 18A
Fig. 18B
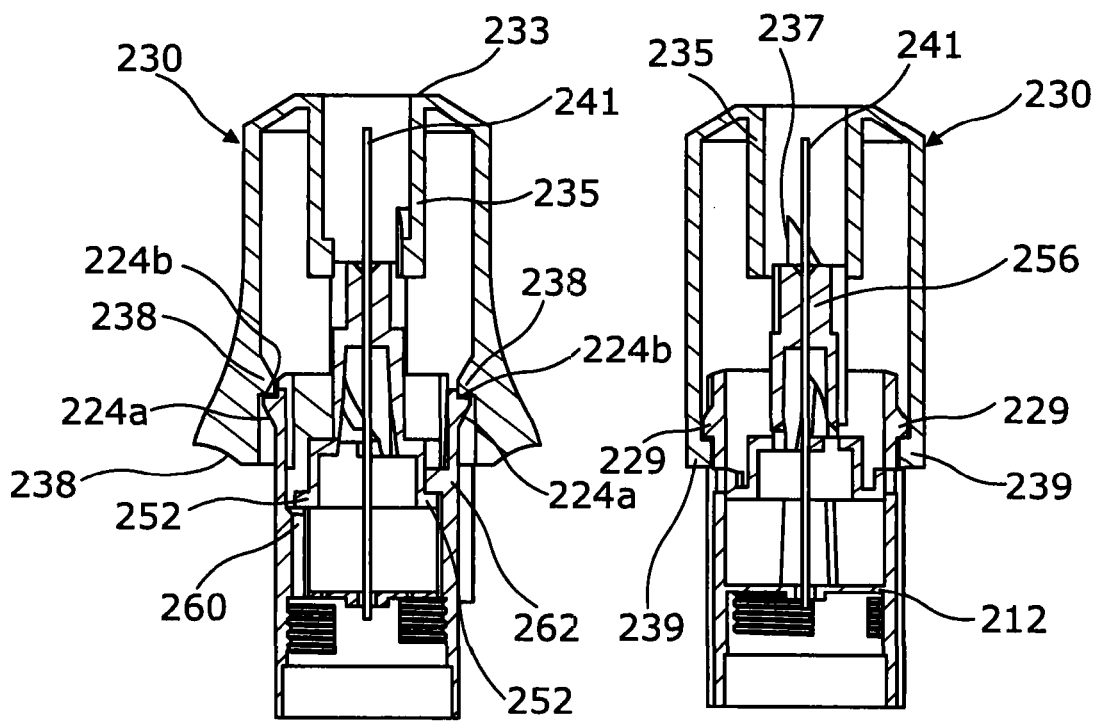
Fig. 19A
Fig. 19B

NEEDLE ASSEMBLY WITH NEEDLE SHROUD AND MOVABLE NEEDLE SUPPORT

CROSS-REFERENCE TO RELATED APPLICATIONS

This application represents the U.S. National Stage of International Application No. PCT/GB2016/051334 filed May 10, 2016 which is incorporated by reference in its entirety and is based on, claims priority to, and incorporates herein by reference in their entireties, British Patent Application Serial Nos. GB 1507981.7, filed May 11, 2015, and GB 1518649.7, filed Oct. 21, 2015.

FIELD OF THE INVENTION

This invention relates to a needle assembly, and in particular, but not exclusively to a single-use disposable needle assembly. Such needle assemblies are typically configured for attachment to an injection device, cartridge or syringe.

BACKGROUND OF THE INVENTION

Injection devices, such as the Owen Mumford Autopen®, are commonly used by patients to self-administer injections of medicament. Such devices are typically provided in a pen-like body which contains, defines or receives a cartridge or syringe of medicament. The injection device generally comprises a delivery mechanism which is arranged to dispense the medicament via a needle in response to a user pressing a button or trigger.

As many such injection devices are arranged to be either reusable (i.e. the cartridge of medicament can be replaced) or to deliver a plurality of separate injections until the medicament within the device has been fully consumed it is common to arrange the device to receive a disposable, single-use, needle assembly. Such needle assemblies are generally referred to as "pen needles".

Pen needles comprise a body or hub which is configured to be attached to the injection device in use (for example by means of a screw thread or other removable attachment arrangement) and which supports the needle. Typically, the needle is a double ended needle having a forward end for use in penetrating a user's skin and a rearward end which pierces a septum of a cartridge or syringe in the injection device when the pen needle is attached to the device. It will be appreciated that such syringe/cartridge septa are self-sealing membranes which can maintain the sealing and sterility of the syringe/cartridge over a number of uses. A removable cap may also be provided which initially covers the needle to provide protection against needle stick injuries and to maintain sterility of the needle (and the needle assembly may initially be sealed within the cap by means of removable sterile packaging).

It is known to provide needle assemblies such as pen needles with a shroud which is arranged to cover the needle after use (and in some cases also prior to use) to reduce the risk of accidental needle-stick injuries after use or during disposal of the needle assembly. For example, one form of needle assembly may include a shroud which is arranged to telescope forwardly relative to the hub after use to cover the forward end of the needle. As the needle assembly hub typically has an annular rearwardly extending form (with an internal screw thread interface for attachment to an injection device) and the rearwardly extending portion of the needle is generally of shorter length than the forwardly extending needle portion, the rearward facing end of the needle is partially shrouded by the hub. However, the internal diameter of the rearward portion of the hub is defined by the interface with the injection device and, as such, the applicant has recognised that for at least some devices the resulting opening may be of too large a diameter to prevent the risk of a user's fingertip accidentally coming into contact with the rearward needle tip.

Embodiments of the invention seek to provide improved needle assemblies which may overcome some or all of these problems.

SUMMARY OF THE INVENTION

Accordingly, the invention provides needle assembly for mounting on an injection device comprising:

a body configured to be removably attached to an injection device in use;

a double ended needle supported by the body and extending from a forward tip which faces forwardly relative to the body to a rearward tip which faces rearwardly relative to the body;

a needle shield coupled to the body and arranged for relative axial movement with respect to the body, wherein the needle assembly has an injection configuration, in which the shield is positioned such that the forward tip of the needle projects beyond a forward end of the shield, and a shroud configuration, in which the shield is positioned such that the forward end of the shield extends beyond the forward tip of the needle; and the needle assembly further comprises a needle support fixed relative to the needle, wherein the needle support is captive between the body and the shield;

the needle support being fixed relative to the body when the needle assembly is in the injection configuration and wherein movement of the shield from the injection configuration to the shroud configuration axially displaces the needle support relative to the body.

It will be appreciated that the axial direction of the injection device is generally aligned with (for example parallel with) the axis of the needle.

It will be appreciated that the needle is generally supported by the body in that the body is intended to provide a means of attaching or coupling the needle to an injection device during use (but that the body is not required to directly support the needle).

The needle shield is coupled to the body and the needle support is captive therebetween. The needle support may therefore be internally located within the needle assembly. Advantageously, embodiments may provide an arrangement in which externally only the relative movement of the needle shield relative to the body is visible and the end user does not need to be aware of the additional movement of the needle support. Further, by providing the needle support internally captive between the body and needle shield, the needle assembly may have only a single external coupling when in the shroud configuration after use which may provide a more robust arrangement.

When the needle assembly is in the injection configuration, the shield may be coupled to/engaged with a first part of the body to fix (for example axially restrain) the needle support relative to the body.

In the injection configuration the shield may hold the needle support in a rearward position relative to the body. In the injection configuration, the shield may be coupled to, or engaged with, a rear portion of the body.

When the needle assembly is in the shroud configuration the shield may be coupled to/engaged with a second part of the body to fix (for example axially restrain) the needle support relative to the body.

In the shroud configuration, the shield may hold the needle support in a forward position relative to the body. In the shroud configuration, the shield may be coupled to, or engaged with, a forward portion of the body.

The needle support may be located within a cavity defined between the needle shield and the body When the needle assembly is in the injection configuration, the needle support may be enclosed in a cavity formed between the shield and the body.

The needle support may be an internal component of the needle assembly.

When the needle assembly is in the shield configuration, the needle support and the needle may be enclosed in a cavity formed between the shield and the body.

In the injection configuration the shield may be in a retracted position relative to the body. In the shroud configuration the shield may be in an extended position relative to the body.

In the injection configuration, the needle support may be entirely located with in a recess in the body. In the injection configuration, the needle support may be entirely located with in a recess in the forward portion of the body. The needle support may be located within the body such that it is not visible when the needle assembly is in use. The needle support may move forwardly within the recess as the needle assembly moves to its shroud configuration.

The needle support may surround an intermediate portion of the needle. The needle support may be mounted within the body. The needle support may comprise a collar extending around an intermediate portion of the needle. The needle may be embedded within the needle support. The needle may be secured within the needle support by any convenient means (for example by adhesive). The needle support may, for example, be over-moulded onto the outer surface of the needle. The needle support may comprise a generally axially extending element extending around the needle.

A portion of the needle support, for example a rearward portion, may resiliently engage the body when the needle assembly is in the injection configuration. For example the needle support may include a retention feature (for example a catch or detent) which resiliently engages a portion of the body. The retention feature may for example resiliently engage an aperture in the body (for example an aperture through which the needle extends in the injection configuration). The retention feature on the needle support may engage forwardly extending arms or walls provided inside the body. The needle support may be captive between the body and the shield. When the needle assembly is in the injection configuration, the needle support may be axially restrained between the body and the needle shield.

The needle support may be mounted within the body. The needle support may be mounted inside forward housing portion of the body in the injection configuration. The needle support may be entirely mounted within a recess formed by the body in the injection configuration. The needle support may be mounted so as to contact a rear wall of the forward housing portion in the injection configuration. The needle portion may be prevented from moving within the body in the injection configuration. The needle support may be restrained against rotation within the body in the injection configuration.

The shield and needle support may be provided with cooperating interconnecting features. The interconnecting features may be arranged to control the relative (axial) position of the needle support and shield. The interconnecting features may determine or limit the axial position of the support and shield. The interconnecting features may comprise a stop on one of the shield or needle support which interacts with a projection on the other of the needle support or shield. The stop may for example be formed by an end of a slot (in which the projection is received). The stop may comprise a rear facing surface on one of the shield or needle support which abuts with a projection on the other of the needle support or shield.

The interconnecting features may allow the shield to initially move axially relative to the needle support and body (for example to move forwardly). This initial movement may be towards the final position of the shield in the shrouded configuration. Upon reaching an intermediate position, the interconnecting features may engage to axially couple or fix the needle support relative to the shield. The interconnecting features may engage to axially fix the needle support relative to the shield. Accordingly, further movement of the needle shield (i.e. towards the final shroud position) may cause resulting movement of the needle support (and, therefore, the needle) relative to the body. For example, the movement of the needle support may occur when the projection of the interconnecting features reaches the stop (after which further forward movement of the shield may act to draw the support forward).

It will be appreciated that the arrangement of the interconnecting features (for example the axial extent of the slot) may be selected to sequence the movement of the shield and needle/needle support between the injection and shroud configurations. For example, movement of the shield to the intermediate position relative to the needle support may be sufficient to ensure the forward end of the shield extends beyond the forward tip of the needle (i.e. such that the forward tip is safely shrouded). Subsequent movement to the shroud configuration may act to shield rearward tip.

The interconnecting features may allow the shield and needle support to initially move axially relative to the body, for example to move forwardly. This movement may be towards the final axial position of the needle support, relative to the body. Upon reaching an intermediate position the interconnecting features engage to axially couple the needle support relative to the body. The interconnecting features may engage to axially fix the needle support relative to the shield. Accordingly, further movement of the needle shield (i.e. towards the final shroud position) may cause movement of the needle shield relative to both the body and the needle support.

The axial movement of the needle support may be arrested or stopped when the projection of the interconnecting features reaches the stop (after which further forward movement of the shield results in the shield moving alone).

Movement of the shield to the intermediate position relative to the body may be sufficient to ensure that the rear end of the needle moves to a safe position. Movement of the shield to the intermediate position may ensure that the rear end of the needle moves to a position beyond a radial wall provided in the body.

A stop may be provided on the body to limit forward movement of the needle support. The stop may limit the forward movement of the needle support in the shroud configuration. Thus, in the shroud configuration the needle support may be held in a first axial direction (for example rearwardly) by the needle shield and held the opposing axial direction (for example forwardly) by the body.

The body may include a radial wall. The radial wall may define a separation between a rearward portion configured for removable attachment to an injection device and a forward portion associated with the shield. The wall may include an aperture through which the rearward portion of the needle projects in the injection configuration (and which may also be resiliently engaged by the needle support). In the shroud configuration the rearward end of the needle is forward of the radial wall. Thus, the radial wall may provide a shielding function.

The body may comprise a rearward hub configured for removable attachment to an injection device and a forward housing. For example, the rearward hub may comprise an internal screw thread. The rearward hub and forward housing may be connected together in use (for example during manufacture of the needle assembly). For example the body portions may have a snap fit engagement. The shield and needle support may be captive between the rearward hub and forward housing when the needle assembly is assembled. The shield and the needle support may, for example be captive between the radial wall of the body and a forward component of the housing (for example a slot). The needle support may be retained indirectly (i.e. via the needle shield).

The body may comprise a forward housing portion having at its rear end a hub portion, the hub portion being configured for attachment to an injection device. The hub portion may be formed integrally with the forward housing portion, or may be connected to the rear end of the housing via any suitable means, for example via a snap fit connection.

Upon movement from the injection configuration to the shroud configuration, the needle assembly may lock into the shroud configuration. For example, a snap fit arrangement may prevent reverse movement of the needle shield relative to the body. The needle shield may lock in position when the needle assembly is moved into the shrouded configuration. An audible and/or tactile indication may be provided upon locking of the needle shield. For example, the audible and/or tactile indication may be provided when the needle assembly is in the shroud configuration. The needle assembly may further include a visual indication when the needle assembly is in the shrouded configuration. A visual indicator may be provided on a portion of the shield or body which is only visible when the needle assembly is in the shrouded configuration.

The shield and body may be provided with cooperating features comprising at least one latching element provided on one of the shield or the body and at least one corresponding engagement feature provided on the other of the shield and the body. The latch may move into a latched position when the shield is in the shrouded configuration. The latch may comprise at least one resilient barb or finger. A portion of the shield may pass over the latch as the shield moves to the shroud configuration such that the latch may snap into position behind the portion of the shield. The latch may for example be provided in a slot of the body into which a portion of the shield is received.

The latching element may comprise one or more tabs. The tabs may be resiliently deformable. The corresponding engagement feature may comprise corresponding projections. The projections may have a sloped surface and a stepped surface to engage the tab, such that as the latching element travels over the sloped surface, it is forced or deflected outwards and then as it reaches the stepped surface it snaps inwards. The latching element may comprise one or more inwardly projecting tabs provided on the shield, and the corresponding engagement feature may comprise one or more corresponding projections provided on the outer surface of the body. Alternatively, the body may be provided with outwardly projecting tabs, and the inner surface of the shield may be provided with corresponding projections.

The shield may be radially captive between at least a portion of the body and at least a portion of the needle support. The shield, body and needle support may be substantially concentric.

In the injection configuration, a portion of the shield may be disposed within the body. The shield may telescope forwardly out of the body during movement to the shrouded configuration.

The shield may further comprise an actuator portion which extends outside the body. The actuator portion may be configured for pushing the shield forward manually in use. The actuator portion may extend generally radially outwardly from the body of the needle assembly (and may, for example, pass through a slot in the body). The actuator portion may provide a rear surface for pushing the shield forward manually in use.

The shield may be mounted telescopically on the body. The shield may be mounted telescopically over the body. The shield may be mounted on the body such that in the injection configuration, the shield substantially covers the body. The shield may be mounted on the body such that in the injection configuration, a forward wall of the shield contacts the forward portion of the body.

In the injection configuration the body may be substantially located within the shield. The shield may telescope forwardly relative to body during movement to the shroud configuration.

At least one actuator portion may be provided on the outer surface of the shield. The actuator portion may be configured for pushing the shield forward manually in use. The actuator portion may extend generally radially outwardly from the body of the needle assembly (and may, for example, pass through a slot in the body). The actuator portion may provide a rear surface for pushing the shield forward manually in use. Two diametrically opposing actuation portions may be provided on the outer surface of the shield.

The shield may be manually operable. The actuator portions may have rear facing surfaces, which in use, are manually urged forward by a user.

According to a further aspect of the invention there may be provided a needle assembly for mounting on an injection device comprising:

a body configured to be removably attached to an injection device in use;

a double ended needle supported by the body and extending from a forward tip which faces forwardly relative to the body to a rearward tip which faces rearwardly relative to the body;

a needle shield coupled to the body and arranged for relative axial movement with respect to the body, wherein the needle assembly has an injection configuration, in which the shield is positioned such that the forward tip of the needle projects beyond a forward end of the shield, and an intermediate configuration in which the rear end of the needle is in a safe position;

a shroud configuration, in which the shield is positioned such that the forward end of the shield extends beyond the forward tip of the needle; and the needle assembly further comprises a needle support fixed to the needle, the needle support being fixed relative to the body when the needle assembly is in the injection configuration; and wherein movement of the shield from the injection configuration to the shroud configuration axially displaces the needle support relative to the body.

The needle support may be captive between the body and the shield. The needle support may therefore be internally located within the needle assembly. The needle support may be mounted within a cavity formed between the shield and the body.

The body may be provided with a radial wall. When the needle assembly is in the intermediate configuration, the rear end of the needle may be in a position forward of the radial wall. The radial wall may provide a shielding function.

According to a further aspect of the invention there may be provided an injection device including a needle assembly in accordance with an embodiment mounted to its forward end.

Whilst the invention has been described above, it extends to any inventive combination of the features set out above or in the following description or drawings.

BRIEF DESCRIPTION OF THE DRAWINGS

FIG. 7A shows an exploded three-dimensional view of a needle assembly according to a second embodiment of the invention;

FIG. 7B shows a three-dimensional view of the needle assembly body of FIG. 7A;

FIGS. 8A and 8B show front and side views of the needle assembly of FIG. 7A in the injection configuration;

FIGS. 9A and 8B show front and side views of the needle assembly of FIG. 7 A in the shrouded configuration;

FIGS. 11A and 11B show cross sectional views of the needle assembly of FIG. 7 A in an intermediate position FIGS. 12A and 12B show cross sectional views of the needle assembly of FIG. 7A in the shrouded configuration;

FIGS. 16A and 16B show cross-sectional views (through perpendicular planes extending through the axial centre line) of the needle assembly of FIG. 13A in the injection configuration;

FIGS. 17A and 17B show cross sectional views of the needle assembly of FIG. 13A in a first intermediate position;

FIGS. 18A and 18B show cross sectional views of the needle assembly of FIG. 13A in a second intermediate position; and FIGS. 19A and 19B show cross sectional views of the needle assembly of FIG. 13A in the shrouded configuration.

DESCRIPTION OF EMBODIMENTS

Figure 1:
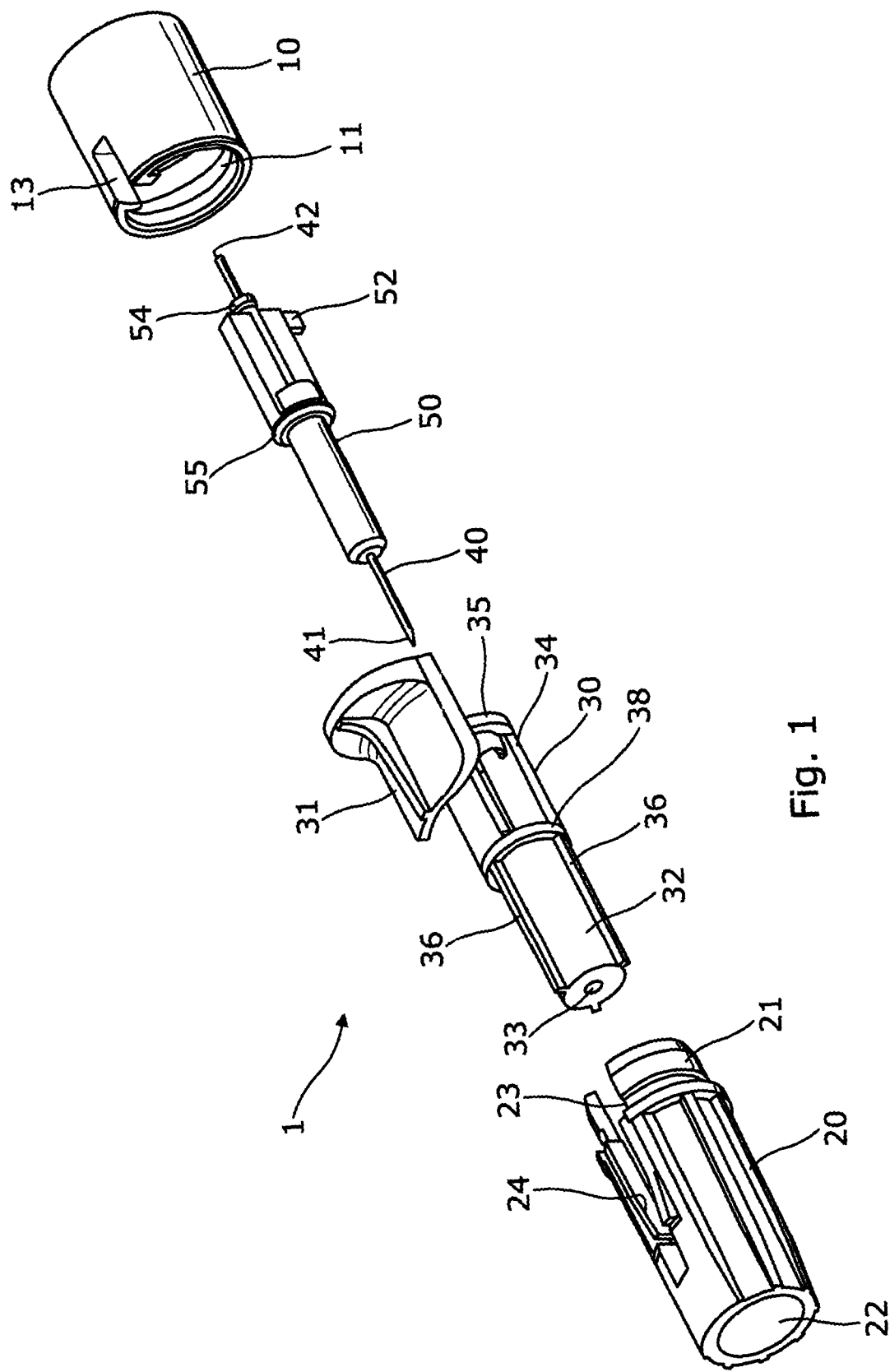
FIG. 1 shows an exploded three-dimensional view of a needle assembly according to a first embodiment of the invention.

In the following embodiments, the terms "forward" and "front" refer to the patient facing end of the needle assembly or component thereof. In other words, the front end of the needle assembly is the end proximal to the injection site during use. Likewise, the term "rear" refers to the non-patient end of the needle assembly or component thereof. In other words, the term "rear" means distant or remote from the injection site during use.

Axial, radial and circumferential are used herein to conveniently refer to the general directions relative to the longitudinal direction of the needle assembly (or components thereof). The skilled person will, however, appreciated that these terms are not intended to be narrowly interpreted (and for example, the needle assembly may have a non-circular and/or irregular form). Typically, regardless of the chosen needle assembly external profile the needle will have a conventional generally cylindrical elongate hollow form and the longitudinal axis of the needle assembly will substantially coincide with (or be parallel to) the axial direction of the needle.

With particular reference to FIGS. 1 to 4, a needle assembly 1 in accordance with a first embodiment comprises a body, formed of a hub 10 and a forward housing 20, a shield 30, a needle 40 and a needle supporting member 50. Each of the components are generally concentrically arranged around the axis of the needle 40.

The hub 10 and forward housing 20 together define a main body of the needle assembly 1 having a generally cylindrical form. A snap fit engagement arrangement is provided between the hub 10 and forward housing 20 in the form of a recess 11 at the forward end of the hub 10 which receives a collar 21 at the rearward end of the forward housing 20.

The forward housing 20 has a generally annular profile with a bore 22 extending through the housing. An axial slot 13/23 is defined in the housing by a first slot portion 23 in the forward housing 20 and a second slot portion 13 in the hub 10. Two resilient members 24 are formed in the sides of the slot and are sloped inwardly into the slot in the forward direction to provide a barbed arrangement.

The hub 10 is provided with a recess 17 at its rearward face which is configured to have a suitable profile for attachment on to the desired injection device. In the illustrated embodiment, the recess 17 is provided with an internal screw thread 18 for engaging a corresponding thread on an injector device. A radially extending wall 12 extends across the hub 10 and separates the recess 17 from the portion 11 to which the forward housing 20 is attached. The radial wall 12 includes an aperture 15 through which the rearward portion of the needle 40 extends in the injection configuration.

The needle shield 30 comprises a cylindrical portion 32 and an actuation member 31. The cylindrical portion 32 extends from a forward end 33 having an aperture through which the forward portion of the needle 40 may project. The outer surface of the cylindrical portion 32 is (optionally) provided with a plurality of external ribs 36 which support and/or align the needle shield against the internal surface of the bore 22 of the housing 20. The rearward section of the cylindrical portion 32 is provided with a pair of circumferentially opposed axially extending slots 34 which extend between a forward 38 and rearward 35 ribs which form stop surfaces at either end of the slots 34.

The actuation member 31 extends generally radially outwardly from the cylindrical portion 32 so as to be outside of the body 10/20. The actuation member 31 is provided with an external profile which is shaped to broadly follow the external shape of the needle assembly and to provide a rearward push surface for use in manually urging the needle shield forward in use. A connecting member 37 extends between the cylindrical portion 32 and the actuation member 31 and has a cross section which is sized to extend through and be received within the slot 13/23 of the body 10/20.

The needle support 50 comprises a collar co-moulded around an intermediate portion of the needle 40. The needle support 50 is rigidly fixed relative to the needle 40 and supports the needle 40 within the needle assembly 1. At the rearward end of the needle support 50 a seat is formed which, in the injection position, abuts the forward surface of the radial wall 12 of the hub 10. A rearward cylindrical extension 54 of the needle support 50 is configured to be received within the aperture 15 in the radial wall 12. The cylindrical extension 54 is provided with a convex outer profile to form a detent such that the cylindrical extension 54 resiliently engages the aperture 15. The rearward portion of the needle support 50 is also provided with an outwardly radially extending finger 52 (immediately forward of the seat). Forwardly of the finger 52 (and in a mid region of the needle support 50) a radial flange 55 is provided around the outer surface of the needle support 50. The radial flange 55 is sized to be received within the axial slots 34 of the shield 30 (and has a tapered forward surface to assist in assembly thereof, but a stepped rearward surface to resist removal after assembly).

Figure 2:
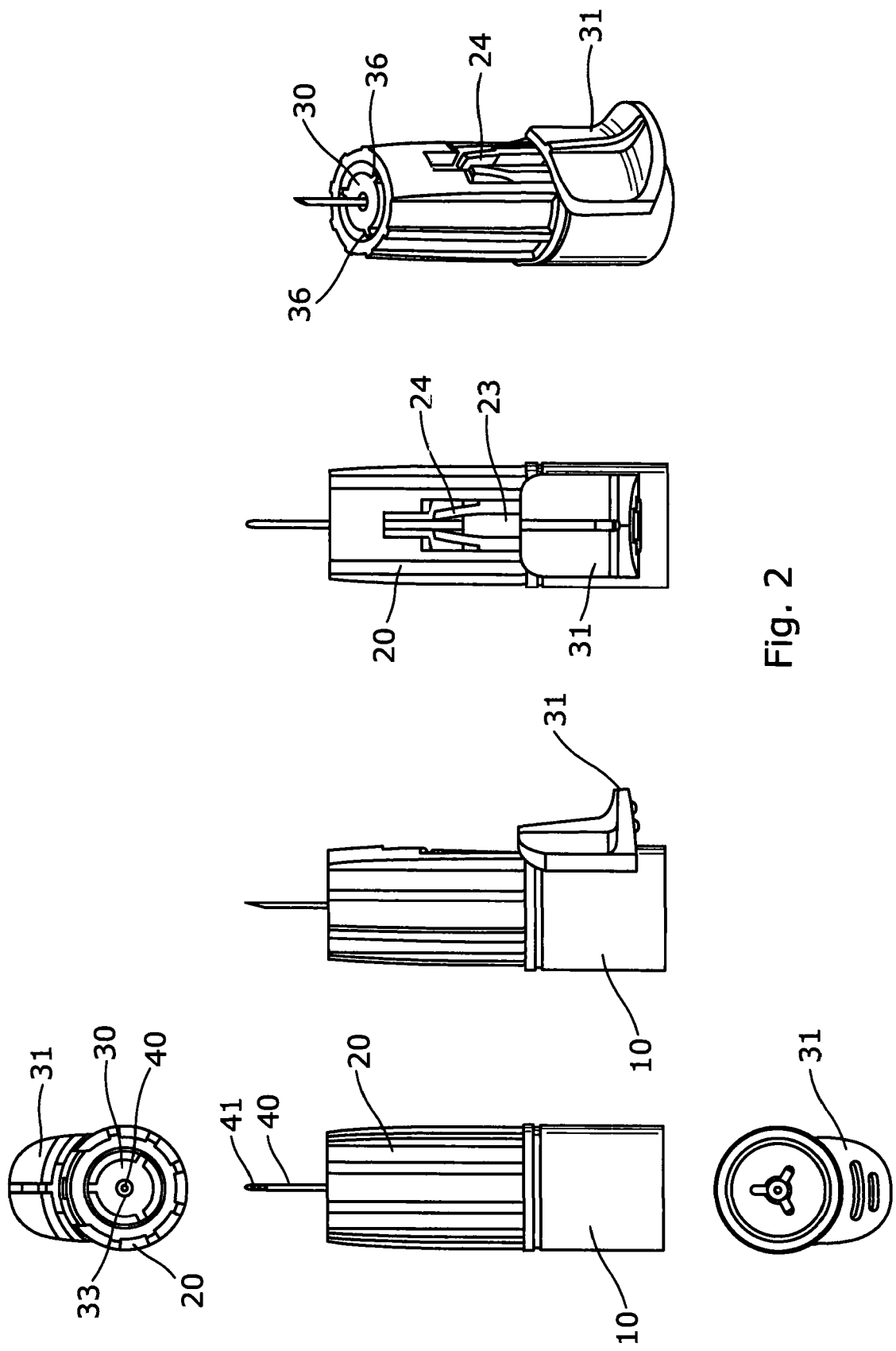
FIG. 2 shows a series of views of the needle assembly of FIG. 1 in the injection configuration.

Operation of the needle assembly 1 will now be described. The needle assembly is supplied in a fully assembled condition in the injection configuration as shown in FIG. 2. Generally the needle will be provided within a protective cap (not shown) with a sterile seal to retain the needle assembly therein. The protective seal is torn away from a rear face of the cap and the needle assembly 1 is attached to an injector device via the screw thread 18 in the rearward recess 17 before the cap is removed. During this connection, it will be appreciated that the rearward tip 42 of the needle 40 will pierce the septum of the injection device.

In the initial, injection configuration, the hub 10 and housing 20 of the body are snap fitted together with the needle 40/needle support 50 and shield 30 captive between the body sections. The shield 30 is retained with the connecting portion 37 in the slot 13/23. The cylindrical portion 32 of the shield 30 is substantially contained within the housing 20. The needle support 50 is seated against the radial wall 12 and resiliently retained by engagement of the convex detent surface of the cylindrical extension 54 in the aperture 15. In this injection configuration the forward tip 41 of the needle 40 is positioned forwardly clear of the front surface 33 of the shield 30 (as well as the front of the housing 20) so is able to be used to penetrate the injection site and deliver an injection.

Figure 5:
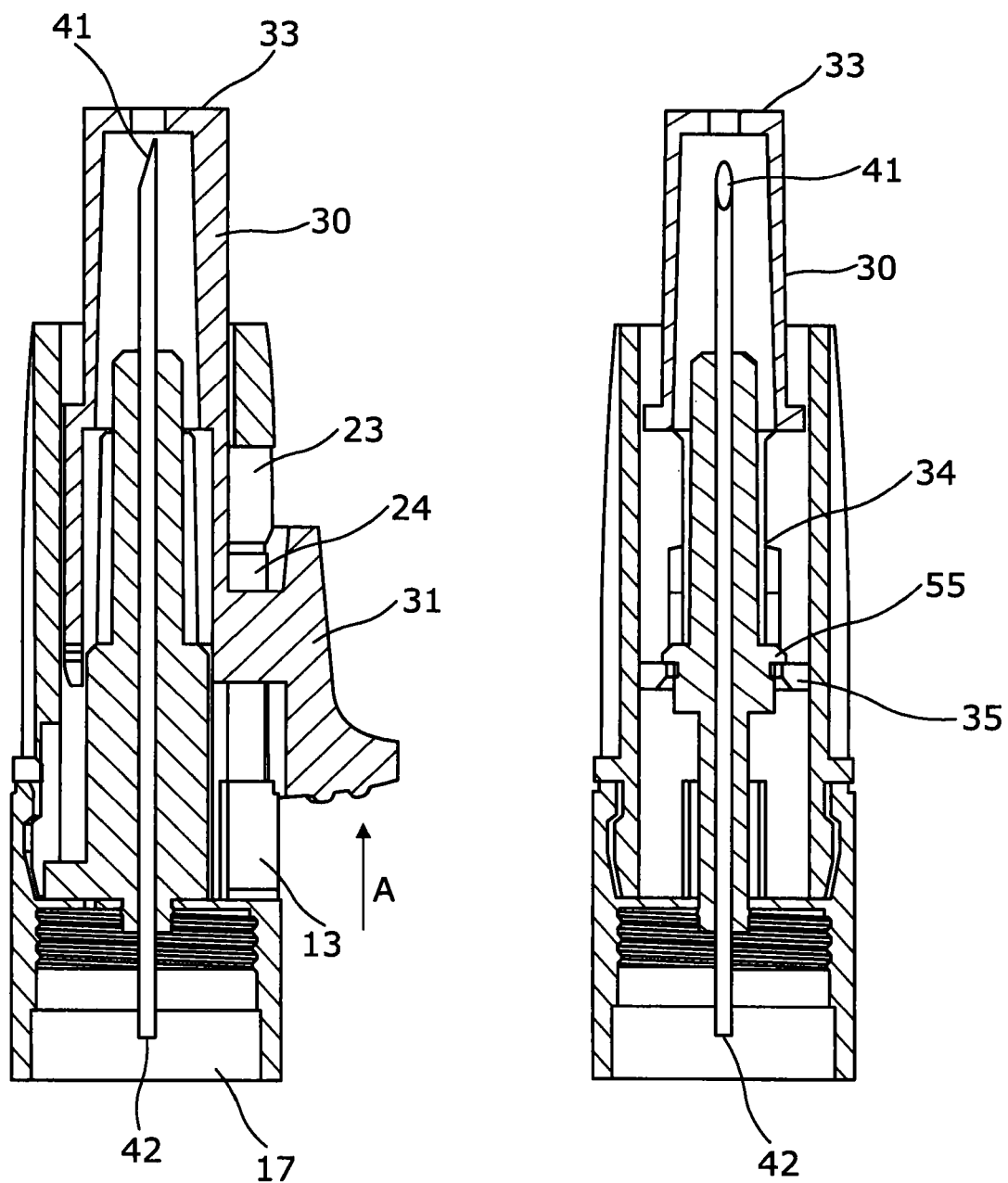
FIG. 5 shows the cross sectional views of FIG. 4 in an intermediate position.

Following completing of the injection (and removal of the needle 40 from the injection site) the actuation member 31 may be manually urged forwardly, as shown by the arrow A, in FIG. 5. This action may be easily carried out by gripping the injection device and pushing on the rearward facing surface of the member 31. The shield 30 slides forwardly relative to the body 10/20 with the connecting portion 37 travelling forward along the slot 13/23. Initially the needle 40 and needle support 50 remain fixed relative to the housing due to the resilient engagement between the aperture 15 and cylindrical extension 54. The initial movement of the shield 30 is sufficient to displace the forward end 33 of the shield beyond the forward needle tip 41.

In this intermediate position, shown in FIG. 5, it will be noted that the forward movement of the shield 30 relative to the needle support 50 results in the radial flange 55 being relatively moved from the forward to rearward end of the axial slots 34. In the intermediate position the rear stop surface 35 of the slots 34 is brought into engagement with the flange 55 such that further forward movement of the shield 30 draws the needle support 50 (and needle 40) forward along with the shield.

Figure 3:
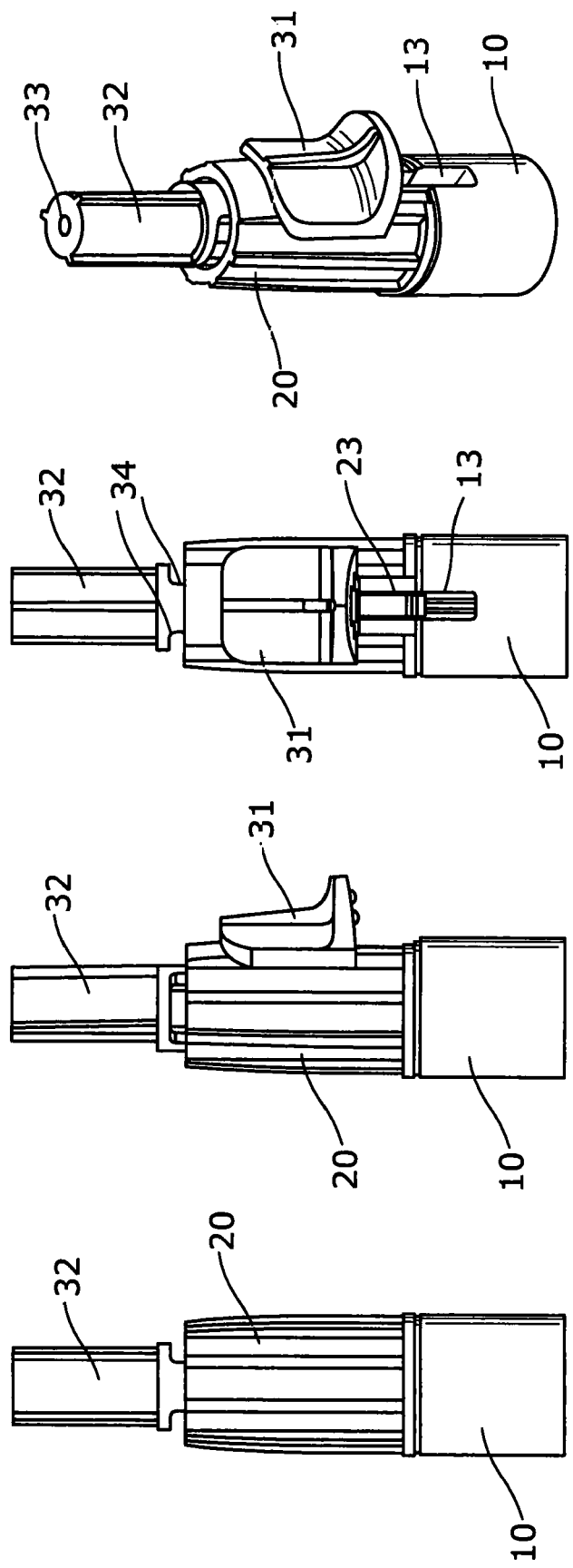
FIG. 3 shows a series of views of the needle assembly of FIG. 1 in the shrouded configuration.
Figure 4:
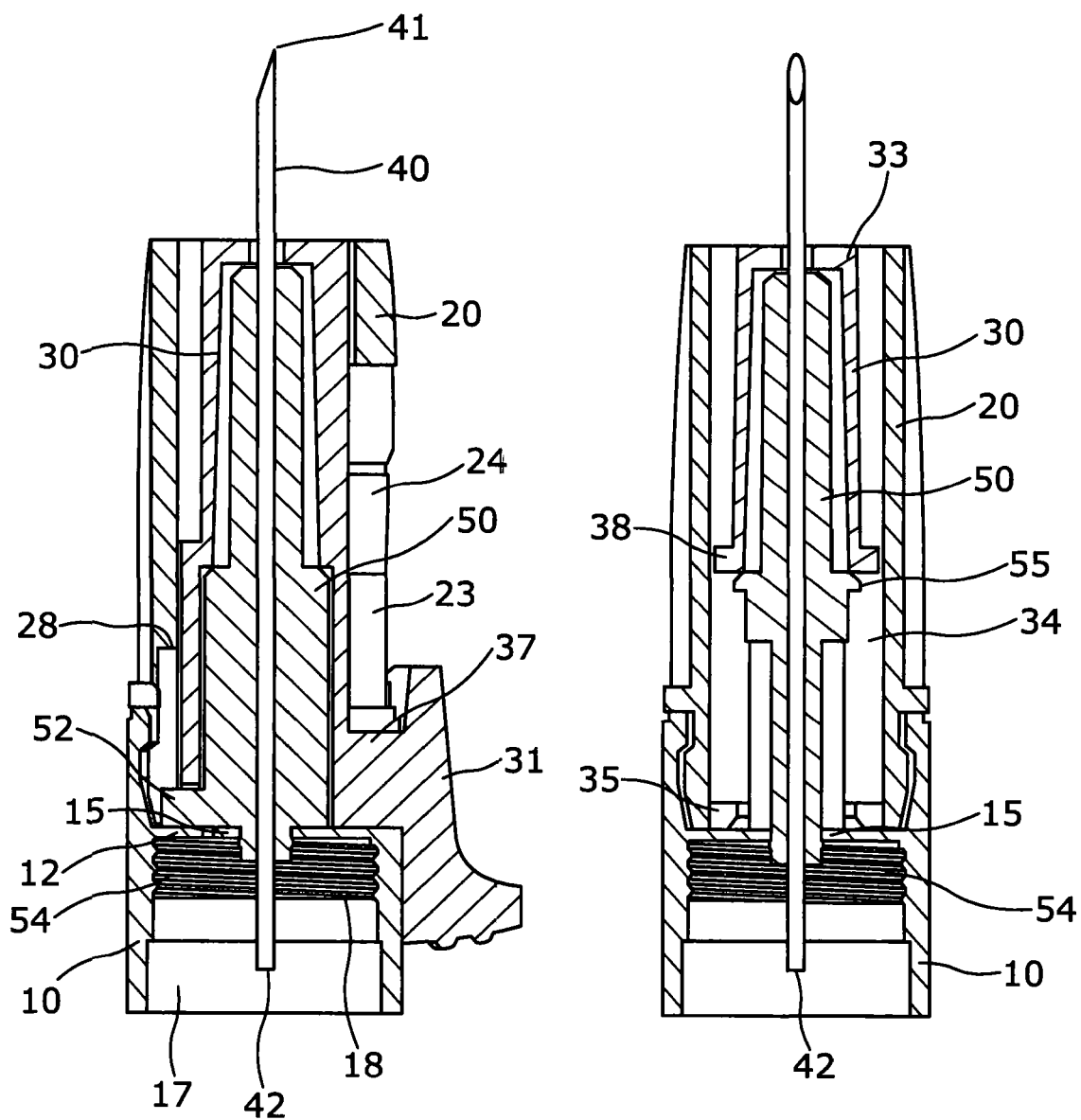
FIG. 4 shows cross sectional views (through perpendicular planes extending through the axial centre line) of the needle assembly of FIG. 1 in the injection configuration.
Figure 6:
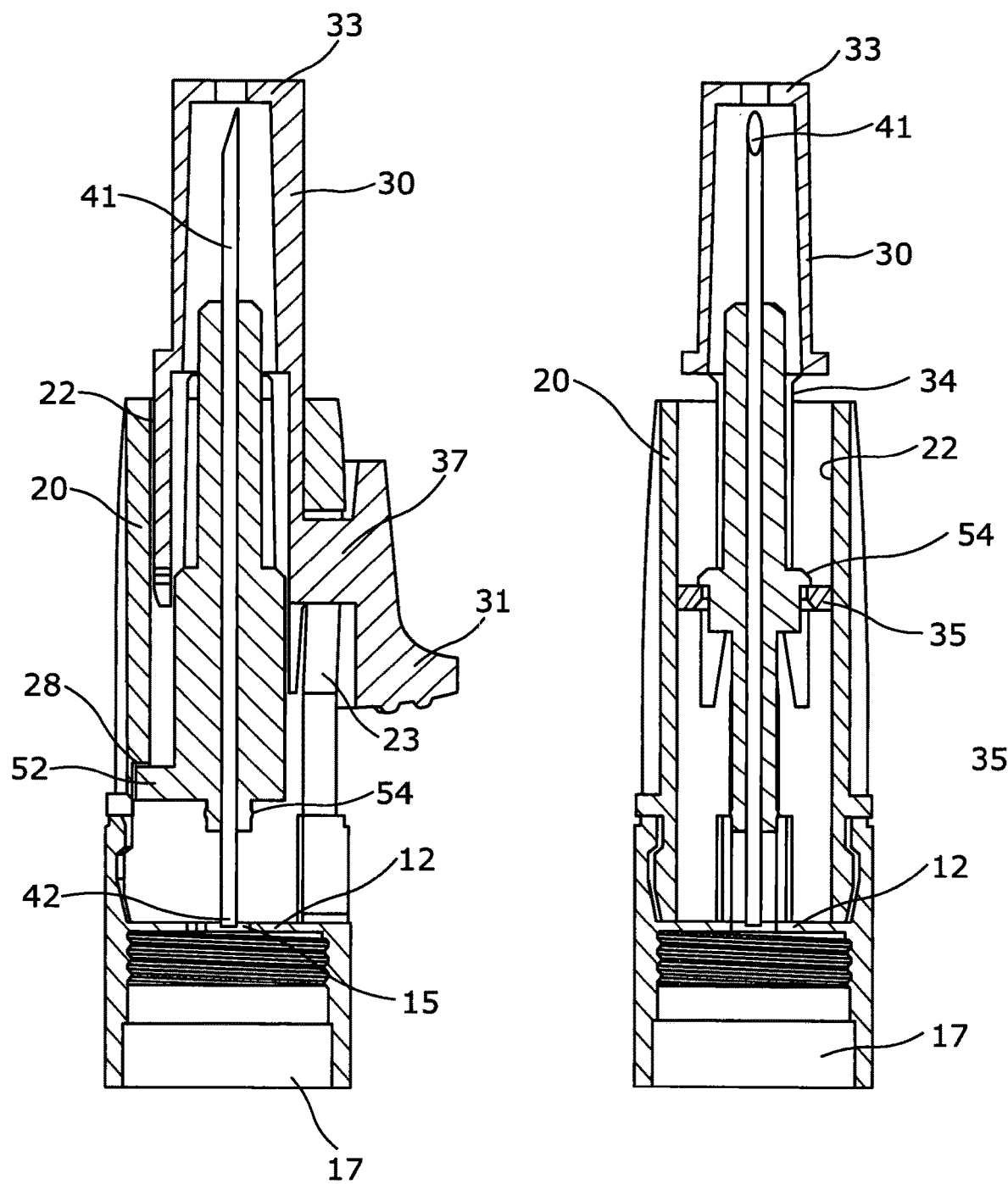
FIG. 6 shows the cross sectional views of FIG. 4 in the shrouded configuration.
Figure 9A:
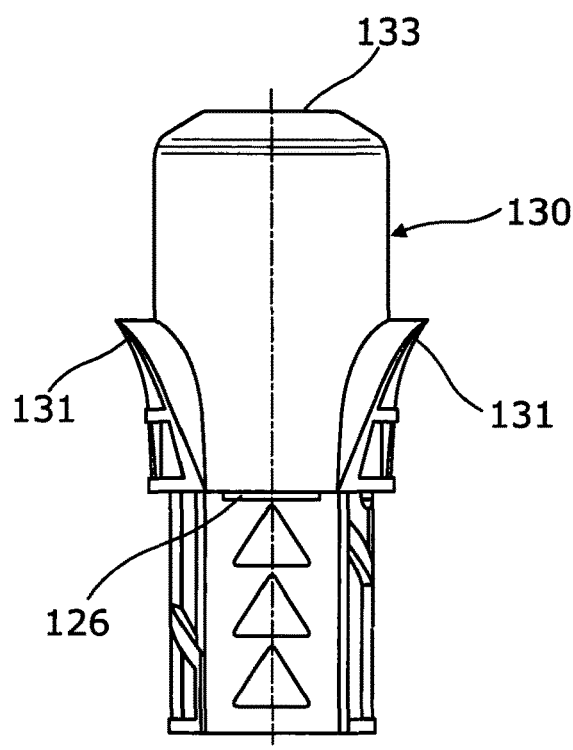
Figure 9B:
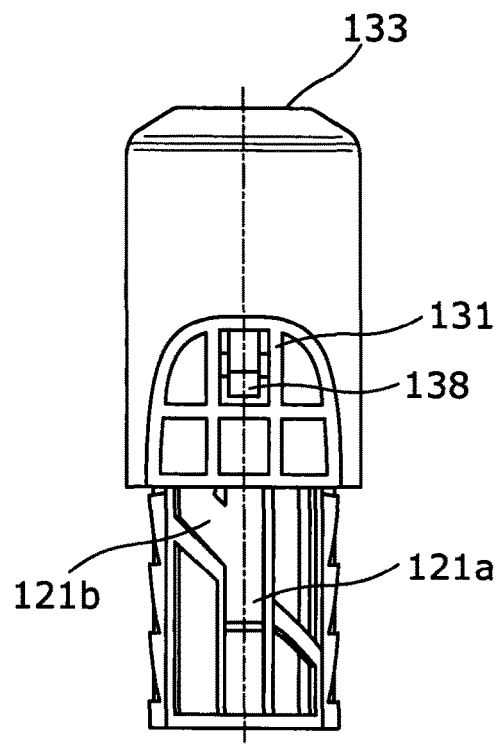

As shown in FIGS. 3 and 6, further forward movement of the shield 30 moves the needle support 50 (and needle 40) forward such that the rearward needle tip 42 positioned forward beyond the radial wall 12. As such the rearward tip 42 is rendered safe. As the shield moves forward it may be noted that the connecting portion 37 moves across the barbed resilient members 24 which are able to deflect circumferentially outwardly to allow the shield to pass into the forwardmost section of the slot 23. Once the connecting portion 37 has fully passed the barbed resilient members 24, the members 24 will snap back into their undeflected position such that the shield 30 is locked into its forward most position and cannot move rearwardly back along the slot 23. This resilient locking action may conveniently be arranged to provide an audible and/or tactile "click" to provide the user with an indication that the shield 30 has locked. It will also be noted that, with the shield 30 in its forward position, the radial finger 52 of the needle support 50 is brought into abutment with a stop surface in the form of a step 28 in the inner surface of the housing 20. This stop prevents the needle support 50 from moving forward relative to the shield 30 when in the shroud configuration and as such prevents the forward tip 41 of the needle 40 moving beyond the forward end 33 of the needle shield 30. Thus, in the shroud configuration, the needle shield 30 is locked in its forward position relative to the body 10/20 and the needle support 50 is held against forward movement by the stop 28 and against rearward movement by the abutment of the cylindrical extension 54 and the rear end 35 of the slot 34. Both tips 41, 42 of the needle 40 are, therefore, safely shrouded and retained within the needle assembly 1 and the needle assembly may be safely disposed of.

The needle assembly may also be provided with a visual indicator (not shown in the Figures) to indicate to the user that the shield 30 has locked in place. For example, the body may be provided with a viewing window which aligns with an indicator element on the shield when the shield is in its forwardmost position. Alternatively, the shield may be provided with markings which are only visible to the user when it has reached its forward position.

FIGS. 7A to 12B show a needle assembly 100 in accordance with second embodiment. The retractable needle assembly includes a body, formed of a forward housing portion 120 and a hub portion 110; a shield 130, a needle 140 and a needle supporting member 150. As with the earlier embodiment, each of these components is concentrically arranged around the axis A of the needle 140 (FIGS. 8A and 8B).

In this embodiment the forward housing portion 120 and the hub portion 110 are formed integrally to provide a body having a generally cylindrical form. The forward housing portion 120 has a generally annular shape with a bore 122. Two diametrically opposite projections 124 are provided at a front end of the forward housing portion 120, the projections extend out from the outer surface of the forward housing portion 120. The projections 124 have a sloped rear surface 124a, and a stepped forward surface 124b. The outer surface of the forward housing portion 120 is provided with an injection completion indication 126. The body is provided on its outer surface with two Y-shaped tracks. Each track has a first axial section 121a and a second dog-legged section, 121b which joins the axial section at its rear end (the function of which is explained below)

Figure 10A:
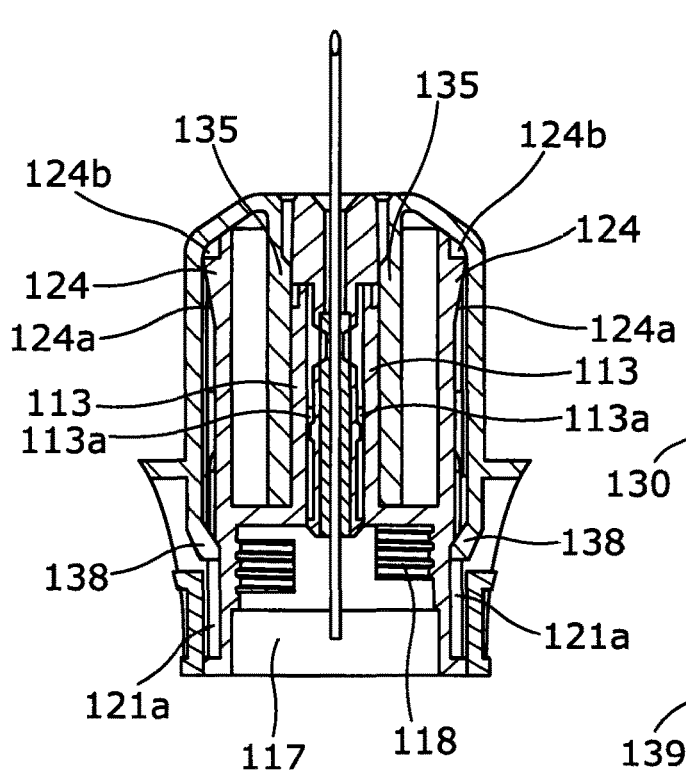
FIGS. 10A and 10B show cross-sectional views (through perpendicular planes extending through the axial centre line) of the needle assembly of FIG. 7 A in the injection configuration.

As shown in FIG. 10A, the hub 110 is provided with a recess 117 at its rearward face which is configured to have a suitable profile for attachment on to the desired injection device. In the illustrated embodiment, the recess 117 is provided with an internal screw thread 118 for engaging a corresponding thread on an injector device. A radially extending wall 112 extends across the hub 110 and separates the recess 117 from the bore 122 of the forward housing portion 120. The radial wall 112 includes an aperture 115 through which a rearward portion of the needle 142 extends in the injection configuration (FIG. 10A). As can be seem in FIG. 7B, curved arms 113 extend forwardly from the radial wall 112 in the bore 122. Arm projections 113a are provided on the inner surface of each arm 113.

Figure 10B:
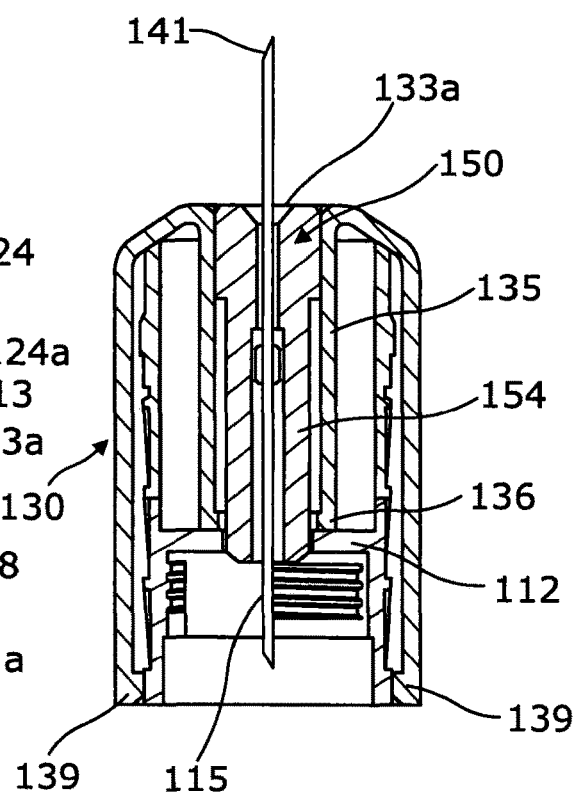

The shield 130 comprises a generally cylindrical outer wall 132 and a forward wall 133 having a central opening 133a. Two actuation members 131 extend outwardly from a rear end 134 of the shield. As can be seen in FIG. 10B, a generally cylindrical inner wall 135 extends rearwardly from the opening 133a. Projecting inwards from the inner surface of the wall 135 are two diametrically opposite lugs 136. When the shield 130 is mounted on the body in the injection configuration (FIG. 10A), the inner wall 135 is located radially outside the arms 113, and the rear end of the inner wall 135 is in contact with the radial wall 112. Two diametrically opposite, resiliently deformable lock-out tabs 138 are provided on the inner surface of the outer wall 132. The tabs 138 are provided in a rear portion of the shield 130. Two diametrically opposite shield projections 139 are provided at the rear end of the shield 130. The shield projections 139 extend radially inwards and are off-set from the tabs 138.

To mount the shield onto the body, each tab 138 is aligned with a corresponding dog-legged track 121b and the shield is pushed rearwards. The tabs 138 follow the path of the track 121b, thus rotating the shield until the tabs are aligned with the axial track 121a. The shield 130 can then be pushed further to its rearward position.

The needle support 150 comprises a collar co-moulded around an intermediate portion of the needle 140. The needle support 150 is rigidly fixed relative to the needle 140 and supports the needle 40 within the needle assembly 100. A forward end 141 of the needle projects forwardly of the needle support 150, and the rear end 142 of the needle projects rearwardly of the needle support 150. The needle support 150 includes a seat 152 and a rear portion 154 extending from the seat 152. First and second (rear) radially extending ribs 154a, 154b are provided on the needle support rear portion 154.

Operation of the needle assembly 100 will now be described. The needle assembly 100 is supplied in a fully assembled condition in the injection configuration as shown in FIGS. 8A and 8B. Generally the needle will be provided within a protective cap (not shown) with a sterile seal to retain the needle assembly therein. As with the above embodiment, the seal is removed and the needle assembly 100 is attached to the injector device via the screw thread.

In the initial, injection configuration (FIGS. 10A and 10B), the shield 130 surrounds the body in its rear position, with each tab 138 located at the rear respective tracks 121a. The shield projections 139 engage corresponding rearward facing sloped surfaces 128 on the body. The forward end 141 of the needle projects forwardly from the shield forward wall 133. The seat 152 of the needle support rests on the forward end of the body arms 113. The shield inner wall 135 is located outside the walls 113 and restrains them against radial deflection. The first ribs 154a on the needle support rear portion 154 are held against forward movement by the arm projections 113a.

Following the injection (and removal of the needle from the injection site), the shield 130 can be moved forward by manually urging the actuation members 131 forwardly. The tabs 138 are cammed outwards by the sloped surfaces 128, and travel along the axial track 121a on the body. The shield 130 moves forward relative to the body and needle support 150, to the intermediate position (shown in FIGS. 11A and 11B. As the inner wall 135 moves forward the lugs 136 contact the seat 152 of the needle support. In the intermediate position, the forward wall 133 of the shield moves beyond the forward needle tip 141.

As the actuation members 131 are urged further forward, the rear end of the wall 135 moves past the arms 113, so that the arms 113 are free to deform outwards and the first rib 154a on the rear portion 154 of the needle support moves past the arm projections 113a. The lugs 136 engage the seat 152 and force the needle support 150 to move forwards. Since the forward movement of the shield 130 draws the needle support 150 forward, the rear tip 142 of the needle moves into a safe position beyond the hub radial wall 112. This means that the rear tip 142 is also rendered safe in the shrouded configuration. The tabs 138 are deformed outwards as they travel over the sloped rear facing surface 124a and they then snap inwards as they reach the stepped surface 124b in the shrouded configuration (FIGS. 12A and 12B), which prevents the shield 130 from moving rearwards again. In the shrouded position (FIGS. 12A and 12B), the shield projections 139 abut stepped surfaces 129 on the body, which prevents further forward movement of the shield. The shield 130 is therefore locked against both forward and rearward movement. The resilient locking action may conveniently be arranged to provide an audible and/or tactile "click" to provide the user with an indication that the shield 130 has locked. The second ribs 154b on the needle support abut the arm projections 113a to prevent the needle support 150 from moving further forward. The needle support 150 is locked this position relative to the shield and body, restrained by the projections 113a and the lugs 136

When the assembly 100 is in the shrouded configuration, the injection complete indication 126 is exposed, providing the user with a visual indication that the shield 130 is locked and is safe.

FIGS. 13 to 19B show a needle assembly 200 in accordance with second embodiment. The retractable needle assembly includes a body, formed of a forward housing portion 220 and a hub portion 210; a shield 230, a needle 240 and a needle supporting member 250. As with the earlier embodiments, the components is concentrically arranged around the axis A of the needle 240 (FIGS. 14A and 14B).

The forward housing portion 220 and the hub portion 210 are formed integrally to provide a body having a generally cylindrical form. The forward housing portion 220 has a generally annular shape with a bore 222. Two diametrically opposite projections 224 are provided at a front end of the forward housing portion 220. The projections extend outwardly and have a sloped rear surface 224a, and a stepped forward surface 224b. The forward housing portion includes exterior axially extending ribs 221, which act to prevent rotation of the shield (as explained later).

The hub 210 (FIG. 16A) is similar to the previous embodiment, having a recess 217 which is configured for attachment to an injection device. In the illustrated embodiment, the recess 217 is provided with an internal screw thread 218. A radially extending wall 212 extends across the hub 210 and separates the recess 217 from the forward housing bore 222. The radial wall 212 includes an aperture 215 through which a rearward portion of the needle 242 extends in the injection configuration (FIG. 16A). As shown in FIG. 13B, two diametrically opposite, axially extending ribs 260 are provided on the inner wall of the bore 222. The ribs 260 extend from the radial wall 212 part way up the inner wall of the bore 222. Provided adjacent to, and spaced forward from the forward end of each rib is a locking tab 262.

The shield 230 comprises a generally cylindrical outer wall 232 and a forward wall 233 having a central opening 233a. Two actuation members 231 extend outwardly from a rear end 234 of the shield. As can be seen in FIG. 16B, a generally cylindrical inner wall 235 extends rearwardly from the opening 233a. Projecting inwards from the inner surface of the wall 235 are two diametrically opposite lugs 236. Also provided on the inner wall, off-set from the lugs 236, are two projections 237 which have forward facing sloped surfaces (visible in FIG. 19B). Two diametrically opposite, resiliently deformable lock-out tabs 238 are provided on the inner surface of the outer wall 232. The tabs 238 are provided in a rear portion of the shield 230. Two diametrically-opposite shield projections 239 are provided at the rear end of the shield 230. The shield projections 239 extend radially inwards and are off-set from the tabs 238.

Figure 13A:
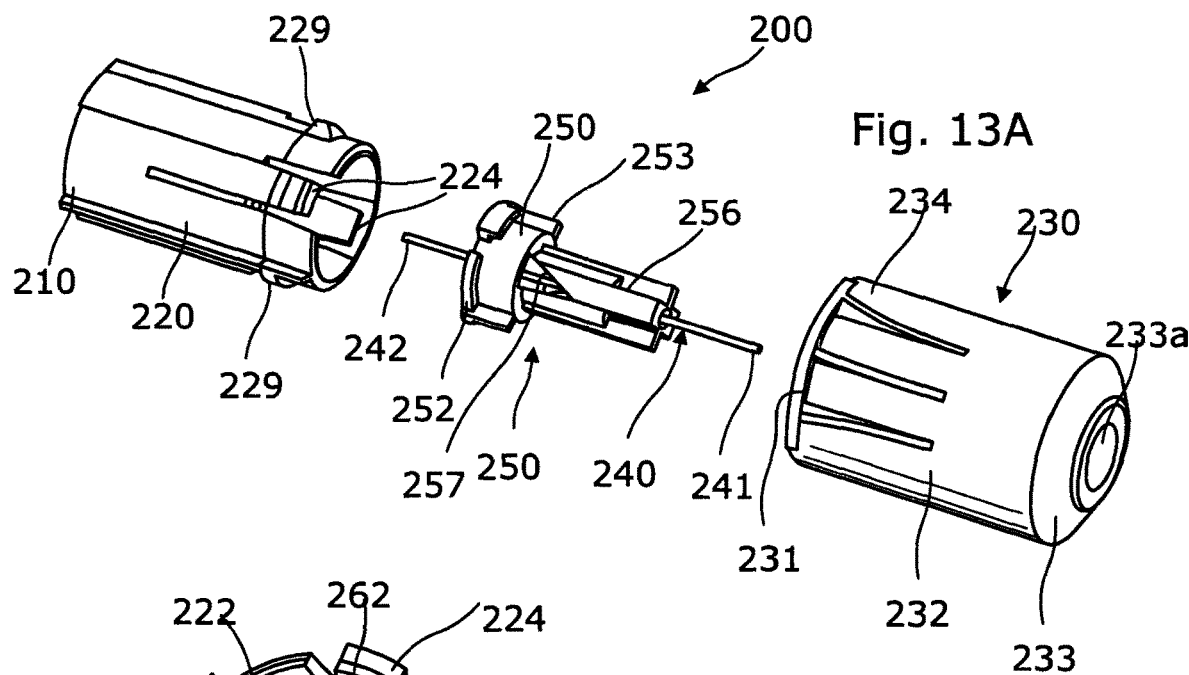
FIG. 13A shows an exploded three-dimensional view of a needle assembly according to a third embodiment of the invention.
Figure 13B:
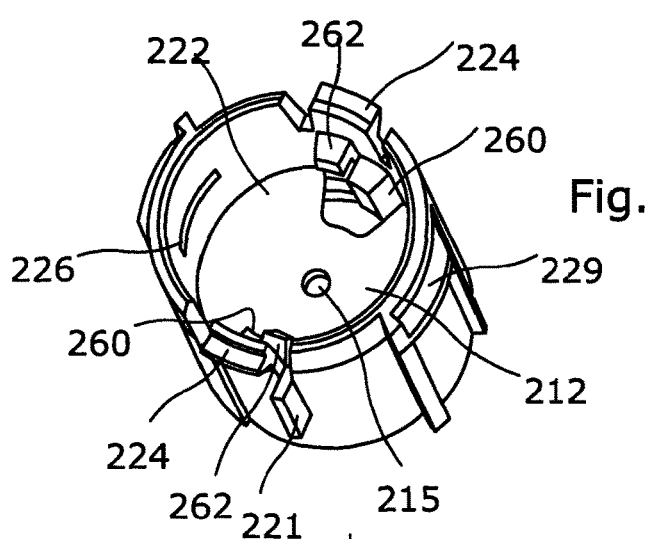
FIG. 13B shows a three-dimensional view of the needle assembly body of FIG. 13A.
Figures 14, 15:
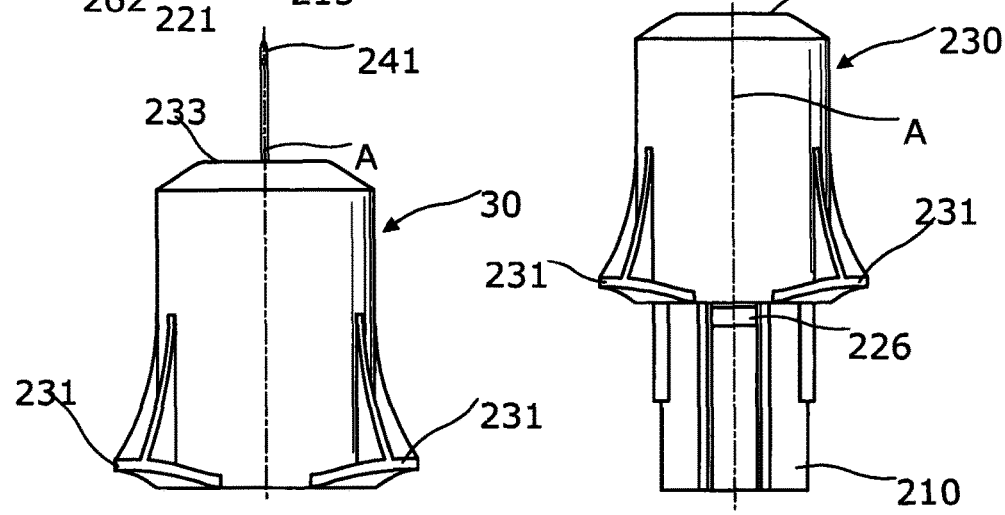
FIGS. 14 and 15 show front views of the needle assembly of FIG. 13A in the injection and shrouded configurations.

The needle support 250 is co-moulded around an intermediate portion of the needle 240 (FIG. 13). The needle support 250 is rigidly fixed relative to the needle 240 and supports the needle 240 within the needle assembly 200. Forward and rear ends 241, 242 of the needle project from the needle support 250. The needle support 250 comprises: a collar 251, a seat 252 formed at the rear of the collar having a larger diameter than the collar 251, and a forward portion 256. In the injection position (FIG. 16A) the rear of the seat 252 abuts the forward surface of the radial wall 212 of the hub 210. Two diametrically opposite, axially extending ribs 253 are provided on the collar 251. The forward portion 256 includes two diametrically projections 257 having rearward facing sloped surfaces 257. The projections 257 are off set from the collar ribs 253. The needle support 250 is mounted into the bore 222 and then rotated so that each collar rib 253 abuts a corresponding rib 260. Operation of the needle assembly 200 will now be described. As with earlier embodiments, the needle assembly 200 is supplied in a fully assembled condition in the injection configuration as shown in FIG. 14. Generally the needle assembly will be provided within a protective cap (not shown) with a sterile seal.

In the initial, injection configuration (FIGS. 16A and 16B), the shield 230 surrounds the body and is in its rearward position. The forward end 241 of the needle projects forwardly from the shield forward wall 233. The shield inner wall 235 is located around the needle support portion 256, and each needle support sloped surface 257 abuts a corresponding shield sloped surface 237. The rear of the needle support seat 252 rests on the hub radial wall 212, and each collar rib 253 abuts a corresponding rib 260. This prevents the needle support from rotating within the bore 222. The exterior ribs 212 on the forward housing portion, engage corresponding elements (not shown) on the interior of the shield 230 to prevent the shield rotating as it moves forward relative to the body.

Following the injection (and removal of the needle from the injection site), the shield 230 can be moved axially by manually urging the actuation members 231 forwardly. The sloped surface 237 of the shield 230 acts on the needle support sloped surface 257, and since the needle support is restrained against rotation by the ribs 260, the needle support 250 moves forward with the shield 230 until a forward surface of the seat 252 contacts the locking tabs 262. The rear tip 242 of the needle moves into a safe position beyond the radial wall 212. This is the first intermediate configuration shown in FIGS. 17A and 17B.

When the seat 252 engages the rear facing locking tabs 262, the collar ribs 253 are forward of the bore ribs 260 which means that the needle support is no longer restrained against rotation. Therefore, as the needle shield 230 is pushed further forward, the shield sloped surfaces 237 act as cam surfaces acting against the needle support sloping surfaces 257 to rotate the needle support 250 until the two sloped surfaces are no longer in contact. This is the second intermediate configuration shown in FIGS. 18A and 18B. In this configuration, the forward surface of the seat 252 abuts the rear faces of the tabs 262 and the rear surface of the seat 252 abuts the forward faces of the ribs 260. This means that the needle support is locked against forward and rearward movement.

As the actuation members 231 are urged further forward, the shield 230 continues to move forward relative to the body and the needle support 250, and the forward wall 133 of the shield moves beyond the forward needle tip 241. The tabs 238 are deformed outwards as they travel over the sloped rear facing surface 224a and they then snap inwards as they reach the stepped surface 224b in the shrouded configuration (FIGS. 19A and 19B), which prevents the shield 230 from moving rearwards again. In the shrouded position (FIGS. 19A and 19B), the shield projections 239 abut stepped surfaces 229 on the body, which prevents further forward movement of the shield. The shield 230 is therefore locked against both forward and rearward movement. The resilient locking action may conveniently be arranged to provide an audible and/or tactile "click" to provide the user with an indication that the shield 230 has locked. In this configuration, the forward surface of the seat 252 abuts the rear faces of the tabs 262 and the rear surface of the seat 252 abuts the forward faces of the ribs 260. This means that the needle support 250 is locked against forward and rearward movement.

When the assembly 200 is in the shrouded configuration, the injection complete indication 226 is exposed, providing the user with a visual indication that the shield 230 is locked and is safe.

Although the invention has been described above with reference to the preferred embodiments, it will be appreciated that various changes or modifications may be made without departing from the scope of the invention as defined in the appended claims. For example, a spring or other biasing means could be provided to automate or assist with the movement of the needle assembly between the injection and shroud configurations (which may simplify operation at the expense of increased complexity of the needle assembly).

The invention claimed is:

1. A needle assembly for mounting on an injection device comprising:

a body configured to be removably attached to an injection device in use;

a double ended needle supported by the body and extending from a forward tip which faces forwardly relative to the body to a rearward tip which faces rearwardly relative to the body;

a manually operable needle shield coupled to the body and arranged for relative axial movement with respect to the body, wherein the needle assembly has an injection configuration, in which the shield is positioned such that the forward tip of the needle projects beyond a forward end of the shield, and a shroud configuration, in which the shield is positioned such that the forward end of the shield extends beyond the forward tip of the needle; and the needle assembly further comprises a needle support fixed to the needle, wherein the needle support is internally captive between the body and the shield;

the needle support being fixed relative to the body when the needle assembly is in the injection configuration;

wherein movement of the shield from the injection configuration to the shroud configuration axially displaces the needle support relative to the body, and wherein the shield is mounted telescopically on the body, wherein in the injection configuration the body is substantially located within the shield, and wherein the shield telescopes forwardly relative to body during movement to the shroud configuration.

2. A needle assembly as claimed in claim 1, wherein the needle support comprises a collar extending around an intermediate portion of the needle.

3. A needle assembly as claimed in claim 1, wherein a rearward portion of the needle support resiliently engages the body when the needle assembly is in the injection configuration.

4. A needle assembly as claimed in claim 3, wherein, when the needle assembly is in the injection configuration, the needle support is axially restrained between the body and the needle shield.

5. A needle assembly as claimed in claim 1, wherein the shield and the needle support are provided with cooperating interconnecting features which control the relative position of the needle support and shield.

6. A needle assembly as claimed in claim 5, wherein the interconnecting features comprise a stop on one of the shield or needle support which interacts with a projection on the other of the needle support or shield.

7. A needle assembly as claimed in claim 5, wherein the interconnecting features allow the shield to initially move axially relative to the needle support and body, and upon reaching an intermediate position the interconnecting features engage to axially couple the needle support relative to the shield such that further movement of the needle shield causes movement of the needle support relative to the body.

8. A needle assembly as claimed in claim 7, wherein movement of the shield to the intermediate position relative to the needle support is sufficient to allow the forward end of the shield to extend beyond the forward tip of the needle.

9. A needle assembly as claimed in claim 5, wherein the interconnecting features allow the shield and needle support to initially move axially relative to the body, and upon reaching an intermediate position the interconnecting features engage to axially couple the needle support relative to the body such that further movement of the needle shield causes movement of the needle shield relative to the body and the needle support.

10. A needle assembly as claimed in claim 9, wherein movement of the shield to the intermediate position relative to the body is sufficient to ensure that the rear end of the needle moves to a safe position.

11. A needled assembly as claimed in claim 10, wherein in the shroud configuration the rearward end of the needle is forward of the radial wall.

12. A needle assembly as claimed in claim 1 wherein the body comprises a stop for limiting forward movement of the needle support.

13. A needle assembly as claimed in claim 1 wherein the body includes a radial wall which separates a rearward portion configured for removable attachment to an injection device and a forward portion associated with the shield, the wall including an aperture through which the rearward portion of the needle projects in the injection configuration.

14. A needle assembly as claimed in any claim 1, wherein the body comprises a rearward hub configured for removable attachment to an injection device, and a forward housing.

15. A needle assembly as claimed in claim 14, wherein the rearward hub and forward housing are connected together in use with the shield and needle support captive therebetween.

16. A needle assembly as claimed in claim 1, wherein the shield and body are provided with cooperating features comprising at least one latching element provided on one of the shield or the body and at least one corresponding engagement feature provided on the other of the shield and the body; wherein the latch moves into a latched position when the shield is in the shroud configuration.

17. A needle assembly as claimed in claim 1 wherein the shield is radially positioned between at least a portion of the body and at least a portion of the needle support.

18. A needle assembly as claimed in claim 1, wherein at least one actuator portion is provided on the outer surface of the shield.

19. An injection device including a needle assembly according to claim 1 mounted to its forward end.

20. A needle assembly for mounting on an injection device comprising:

a body configured to be removably attached to an injection device in use;

a double ended needle supported by the body and extending from a forward tip which faces forwardly relative to the body to a rearward tip which faces rearwardly relative to the body;

a manually operable needle shield coupled to the body and arranged for relative axial movement with respect to the body, wherein the needle assembly has an injection configuration, in which the shield is positioned such that the forward tip of the needle projects beyond a forward end of the shield, and an intermediate configuration in which the rear end of the needle is in a safe position;

a shroud configuration, in which the shield is positioned such that the forward end of the shield extends beyond the forward tip of the needle; and the needle assembly further comprises a needle support fixed to the needle, the needle support being fixed relative to the body when the needle assembly is in the injection configuration and wherein movement of the shield from the injection configuration to the shroud configuration axially displaces the needle support relative to the body, and wherein the shield is mounted telescopically on the body, wherein in the injection configuration the body is substantially located within the shield, and wherein the shield telescopes forwardly relative to body during movement to the shroud configuration.

* * * * *